United States Patent [19]

Stewart et al.

[11] Patent Number: 4,911,687
[45] Date of Patent: Mar. 27, 1990

[54] COMPACT TAMPON APPLICATOR WITH SNAP-ACTION HINGED PANELS

[75] Inventors: A. Eugene Stewart, Ringwood; Joseph Albora, River Edge, both of N.J.

[73] Assignee: Playtex Family Products, Inc., Stamford, Conn.

[21] Appl. No.: 234,856

[22] Filed: Aug. 22, 1988

[51] Int. Cl.⁴ .............................................. A61F 15/00
[52] U.S. Cl. ....................................... 604/15; 604/11; 604/16
[58] Field of Search ........................ 604/11, 12, 13, 14, 604/15, 16, 17, 18, 330, 328, 55, 59, 60

[56] References Cited

U.S. PATENT DOCUMENTS

| | | |
|---|---|---|
| 2,829,646 | 8/1952 | Kurkjian . |
| 3,101,713 | 2/1961 | Sargent ................................. 604/16 |
| 4,276,881 | 7/1981 | Lilaonitkul . |
| 4,286,595 | 9/1981 | Ring . |
| 4,411,647 | 10/1983 | Sakuri et al. ........................ 604/16 |
| 4,479,791 | 10/1984 | Sprague . |
| 4,543,086 | 9/1985 | Johnson . |
| 4,676,773 | 6/1987 | Sheldon . |
| 4,726,805 | 2/1988 | Sanders, III . |

FOREIGN PATENT DOCUMENTS 2060396  5/1981  United Kingdom .

Primary Examiner—Richard J. Apley
Assistant Examiner—Rachel M. Healey
Attorney, Agent, or Firm—Stewart J. Fried

[57] ABSTRACT

A compact and short tampon applicator is formed of an outer barrel which surrounds a tampon-holding inner tubular plunger which is slidable within the outer barrel. A portion of the wall of the plunger defines a pair of hinged panels which snap into the interior of the plunger in response to an inwardly directed radial force. This inward force is supplied by a tab on the barrel, once the plunger has been retracted sufficiently out of the barrel to register the hinged panels with the tab. The applicator is readied for use by retracting the plunger rearwardly behind the tampon, sufficiently to cause the hinged panels to engage the tab on the inner surface of the barrel to snap into the plunger. After insertion of the barrel into the catamenial canal, the plunger is pressed inward, back into the barrel, to enable its inwardly snapped panels to engage the rear of the tampon and to eject the tampon through the front of the barrel.

15 Claims, 2 Drawing Sheets

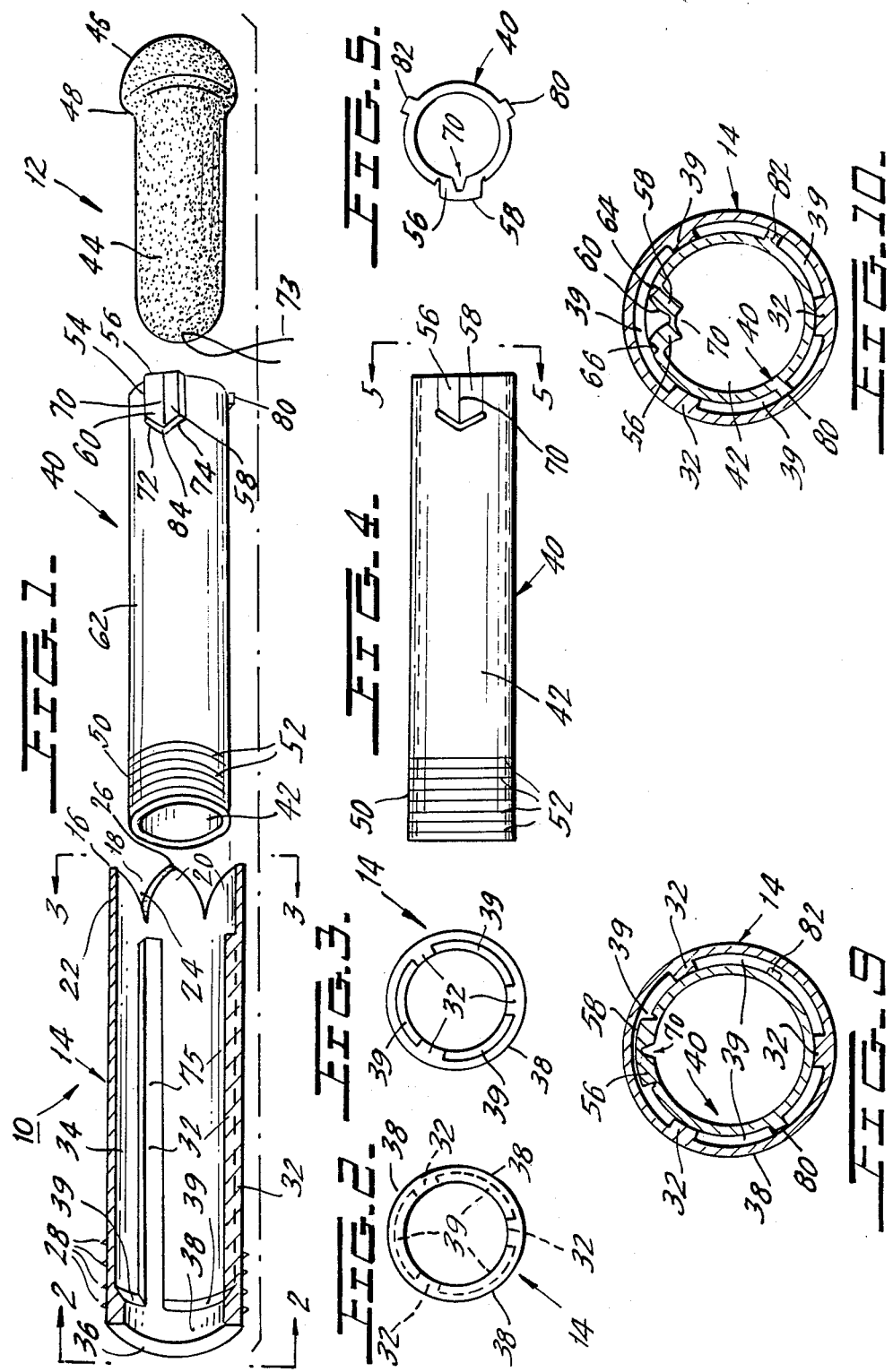

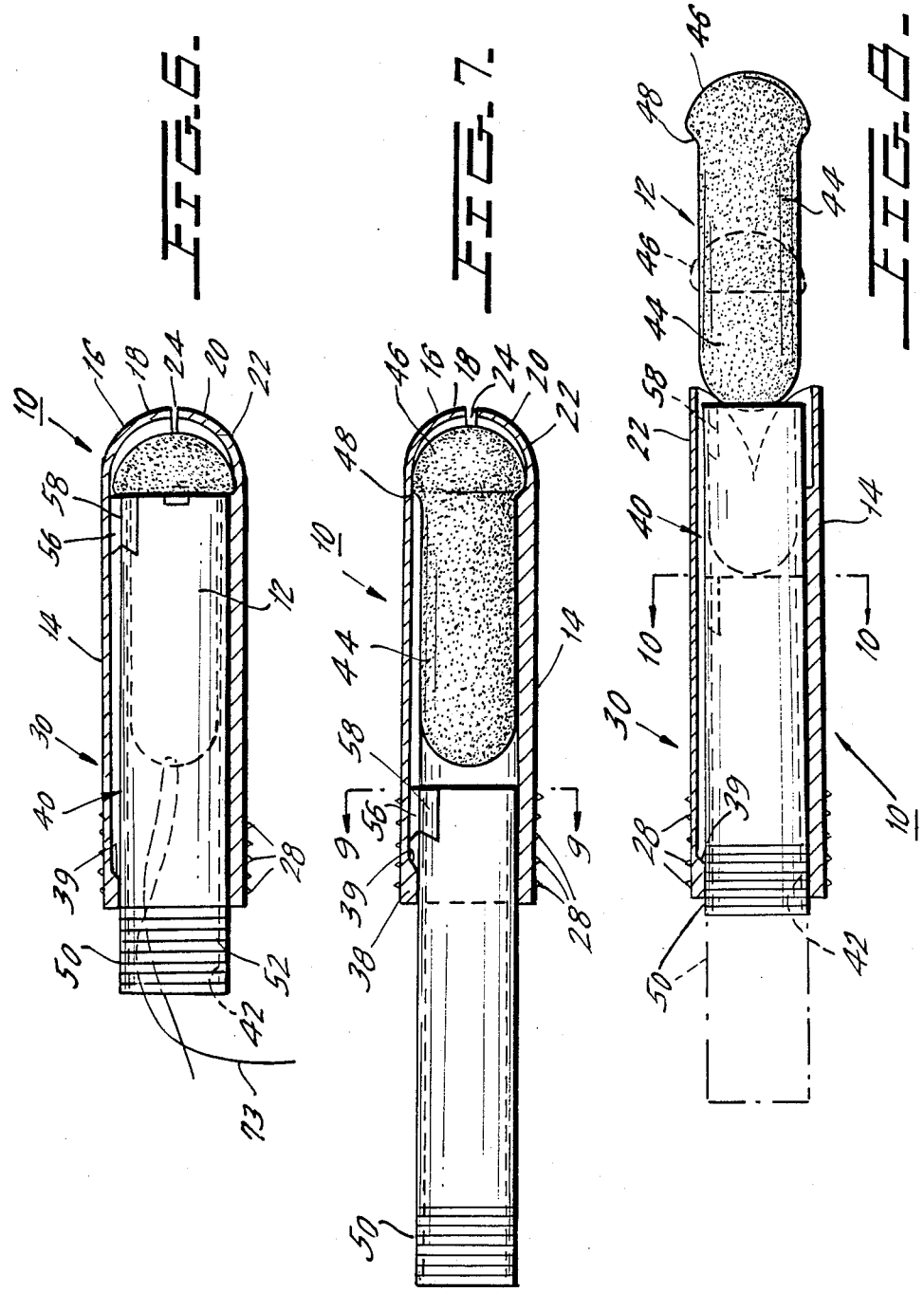

COMPACT TAMPON APPLICATOR WITH SNAP-ACTION HINGED PANELS

BACKGROUND OF THE INVENTION

The present invention relates to a tampon applicator and, more particularly to a preferably short and compact applicator in which the tampon is initially positioned within a plunger, and the tampon is ejected from the plunger by first retracting the plunger backward and subsequently moving the plunger forward for ejecting the tampon from the applicator into the catamenial canal.

Different styles of applicators for introducing catamenial tampons intravaginally are available. Manufacturers strive to make their applicators simpler, easier to use and less expensive in order to obtain even small advantages over competitive devices. A small saving in the manufacture of an applicator can translate into substantial profits in view of the high annual volume of tampon applicators.

The present invention is generally directed to a tampon applicator which has an outer, cylindrical, barrel which holds an absorbent tampon for being ejected into the catamenial canal, wherein the tampon is ejected by a cylindrical plunger that is positioned behind the tampon in the barrel. The plunger diameter is somewhat smaller than that of the barrel and the plunger slides within the barrel for ejecting the tampon out the front of the barrel. After the tampon has been emplaced in the catamenial canal, the applicator is withdrawn and discarded.

More specifically, the present invention is modeled after the type of compact applicator described in U.S. Pat. No. 4,286,595 to Ring (the '595 patent) which is about one-half as long as conventional applicators. That short length applicator has the tampon initially disposed within the plunger, and permits almost the entire body of the plunger to be received within the barrel. The applicator is readied for use by retracting the plunger behind the tampon. Subsequent forward actuation of the plunger pushes the tampon out of the front of the barrel into the catamenial canal.

The tampon pushing end of the plunger (in the '595 patent) has a set of flexible petals which collapse inwardly behind the tampon, once the plunger has been retracted clear of the tampon. The collapsed petals form a tampon contacting surface which contacts the rear of the tampon for pushing the tampon out the front of the barrel of the applicator.

The tampon contacting surface in the '595 patent is complex and costly to manufacture. The plunger must be formed of flexible material and preferably material which can be thermoset.

SUMMARY OF THE INVENTION

Accordingly, it is a primary object of the present invention to provide a simpler, collapsible, tampon pushing mechanism at the tampon contacting end of the plunger for ejecting a tampon out of a tampon applicator.

It is a further object of the present invention to provide a compact tampon applicator which is simpler to fabricate and use.

It is another object of the present invention to provide a compact tampon applicator which can be readily fabricated of either plastic, cardboard, or of combinations of these materials.

The foregoing and other objects of the invention are realized by a tampon applicator which comprises a barrel and a plunger telescopically slidable within the barrel.

The plunger has an interior defined by a peripheral wall for containing a tampon. The plunger has a tampon pushing end and a gripping end for holding the plunger during ejection of the tampon from the barrel.

At least one panel, and preferably a pair of pivoted, hinged panels are disposed in a cutout in the wall of the plunger, at or near the tampon pushing end. The panels project slightly beyond the outer surface of the peripheral wall of the plunger, and the panels are constructed to snap inwardly into the interior of the plunger in response to a radial, inwardly directed, force applied to them.

The barrel is defined by a peripheral barrel wall. It includes an insertion end to be inserted into the catamenial canal and a barrel grasping end opposite the insertion end. At the grasping end of the barrel, a tab projects from the interior surface of the barrel to engage the hinged panels on the plunger during retraction of the plunger to force the hinged panel(s) to snap into the interior of the plunger.

Preferably, the hinged panels are chevron shaped. They have side edges which are joined by a hinge thereby bearing against one another in a manner that causes the panels to snap into the interior of the plunger in response to an inwardly directed force. Further, several spaced ribs extend longitudinally along the interior surface of the barrel, from near the insertion end to the grasping end. The wall of the plunger slides against the ribs, and the radial height of the ribs is sufficient to create an annular space between the plunger and the interior of the barrel which is large enough to accommodate the raised hinged panels of the plunger. The rib ends also restrain the head of a mushroom shaped tampon in the barrel from sliding rearwardly in the barrel during retraction of the plunger.

One or more end stop tabs may be provided on the plunger, approximately 120° from the centerline of the hinged panels, for preventing the plunger from completely separating from the barrel when almost the entire plunger is withdrawn from the barrel when the applicator is being readied for use.

When the plunger has been retracted and the applicator assembly has been readied for use, there are no discontinuous or irregular surfaces, as may be present in other designs, which would contact the vaginal or pubic region in such a way as might cause pinching or pulling.

Other features and advantages of the present invention will become apparent from the following description of the invention which refers to the accompanying drawings.

BRIEF DESCRIPTION OF THE DRAWINGS

FIG. 1 is a perspective, partially cut away, of a disassembled compact tampon applicator in accordance with the present invention.

FIG. 2 is a cross-section through line 2—2 in FIG. 1.

FIG. 3 is a cross-section through line 3—3 in FIG. 1.

FIG. 4 is a longitudinal, orthogonal view of the plunger portion of FIG. 1.

FIG. 5 is a view as seen from line 5—5 in FIG. 4.

FIG. 6 is a longitudinal cross-section through an assembled tampon applicator according to FIG. 1 with the tampon, plunger and barrel assembled for maximum compactness.

FIG. 7 is a cross-section of the tampon applicator of FIG. 6 with the plunger retracted behind the tampon.

FIG. 8 shows the tampon partially (in phantom) and fully ejected from the barrel.

FIG. 9 is a cross-section through line 9—9 in FIG. 7.

FIG. 10 is a cross-section through line 10—10 in FIG. 8.

DESCRIPTION OF THE PREFERRED EMBODIMENTS

The present invention comprises a tampon applicator 10 which holds and enables insertion within the catamenial canal of an absorbent catamenial tampon or pledget 12 with the aid of a plunger 40.

Tampon applicator 10 is formed of an elongate, generally cylindrical, outer barrel 14 which has a forward end 16 which curves radially inwardly to form a convexly rounded insertion tip 18. As seen in FIG. 6, insertion tip 18 has a general hemispherical dome shape which is formed from triangular petal-like segments 20 which are integrally formed from the forward end region 22 of barrel 14.

The material of which barrel 14 is comprised is not critical, and various materials, such as cardboard and plastics, have been widely used for such barrels. Plastics and particularly thermoplastics are especially suitable for forming an insertion tip that will keep its dome shape and yet permit the segments 20 to uncurl relatively easily into an opening as large as the diameter of barrel 14, in response to a relatively slight pressure exerted on the segments from within barrel 14 by tampon 12. The number, size and shape of these triangular segments are selected to yield an insertion tip of a desired configuration. Preferably, four triangular segments are employed. They are shaped to converge in a manner which minimizes the spaces 24 between the individual segments 20 and forms the desired shape without the segments 20 overlapping along their sides or at their apexes or tips 26. Additionally, the tips 26 are preferably rounded to ease insertion.

To enable a user to obtain a good grip on barrel 14, a plurality of spaced circumferential ribs 28 are provided at the rear gripping region 30 on barrel 14. Alternatively, a series of roughening lines may be scored or stamped into the outer surface of wall 22 of barrel 14 to improve the grip on barrel 14.

Barrel 14 is completed with the formation of several, preferably three, longitudinally extending ribs 32 spaced about 120° apart on the interior surface 34 of barrel 14. The ribs 32 extend front to rear, from about the insertion tip 18 of the barrel 14 to the rear edge 36 of the barrel. Preferably, each rib 32 extends circumferentially over an arc angle of about 15°–20°.

At the rear gripping region 30 of the barrel 14, the spaces between adjacent ribs 32 are occupied by tabs 38 which serve to actuate below-described hinged panels associated with the plunger 40. The radial height of the tabs 38 is about the same as that of the ribs 32. On their side which faces the insertion tip 18, the tabs 38 include tapered steps 39 whose thickness tapers down toward the insertion tip 18.

The plunger 40 is cylindrically shaped and sized to hold in its interior 42 the flexible, absorbent catamenial tampon 12. The tampon 12 is mushroom-shaped and includes a stem 44 of a uniform diameter, slightly smaller than the inner diameter of the plunger 40, and a head 46. The head 46 is dome shaped and sized to fit within the insertion tip 18 of barrel 14. The diameter 48 at the base of the head 46 is slightly larger than the outer diameter of the plunger 40 to permit only the stem 44 to fit in the interior 42 of plunger 40. The head 46 is also large enough to be caught on the inwardly projecting ribs 32 of the barrel 14 to prevent the tampon 12 from sliding back through the barrel during retraction of the plunger 40, to the left in FIG. 1.

The plunger 40 is slidable within barrel 14. The gripping end 50 of the plunger 40 projects slightly beyond the rear edge 36 of barrel 14 and provided with closely spaced circumscribing tabs or score lines 52, similar to the lines/tabs 28 on barrel 14.

At its opposite end, the plunger 40 contains a chevron shaped or V-notch cutout which accommodates a snap-action tampon ejecting structure 54 comprising a pair of chevron shaped pivotable panels 56 and 58. One edge of each of the panels 56 and 58 are hingedly connected to a respective side edge of the cutout in the wall of the plunger 40 at respective hinges 64 and 66. The opposed sides are hingedly connected to each other at hinge 70. The hinged connections along the illustrated cut lines, enable the panels 56 and 58 to snap inwardly into the interior 42 of the plunger 40 to assume the position depicted in FIG. 10.

As seen in FIG. 9, before inward deflection, the outer surfaces 60 of the panels 56 and 58 lie radially beyond the outer surface 62 of the plunger 40. Even a relatively light inwardly directed force applied to the panels 56 and 58 initially compresses hinges 64, 66 and 70 of the hinged panels 56 and 58 against each other which, in turn, causes the panels 56 and 58 to snap into and lock within the interior 42 of the plunger 40. The pointed, chevron defining, side edges 72 and 74 of the hinged panels 56 and 58 face toward the gripping end 50 of plunger 40 and provide smooth initial engagement with the tapered steps 39 on the interior of barrel 14 when the plunger has been retracted far enough.

Preferably, the outer diameter of the plunger 40 is about equal to the diameter of the notional circle defined by the inward facing surfaces 75 of the ribs 32 of the barrel 14. The outer surface of the plunger 40 slides along the surfaces 75 of the ribs 32. Since the hinged panels 56 and 58 project beyond the outer surface of the plunger 40, the plunger 40 must be angularly oriented in the barrel 14 to locate the raised hinged panels 56 and 58 between a pair of the ribs 32.

End stop tabs 80 and 82 project from the outer surface of the plunger 40, being approximately 120 degrees apart and being more or less equidistant from the hinged panels 56 and 58, respectively. The end stop tabs 80 and 82 engage the tabs 38 on the barrel 14 to inhibit an accidental over-retraction of the plunger 40 which may cause the plunger 40 to separate from the barrel 14.

Barrel 14 and plunger 40 of the tampon applicator assembly 10 of the present invention may be constructed of materials such as synthetic polymers, cardboard, other biodegradable materials, or the like. For example, barrel 14 may be formed of relatively more rigid plastic, while plunger 40 is formed of cardboard, or vice versa, or they may be formed of like material. Thermoplastics, and particularly, polyolefins are preferred materials for construction of the tampon applicator of the present invention, with polyethylene being particularly preferred due to its low cost and ease of molding. Thermoplastics are probably best for forming the collapsible insertion tip 20 of barrel 14 of the present invention.

The manufacturing process for barrel 14 and plunger 40 may be in accordance with the teachings of U.S. Pat. No. 3,895,634 assigned to the assignee of the instant application, the contents of which are incorporated by reference. The hinged panels 56 and 58 on the plunger 40 may be formed by injection molding or extruding. The hinges 64, 66 and 70 of the hinged panels 56 and 58 and the chevron-shaped cuts of the panels may be formed during the molding process or subsequently by cutting or by any suitable manufacturing method.

Tampon 12 and plunger 40 are assembled in barrel 14 by being inserted through the initially uncurled segments 20 of the insertion tip 18 of the barrel 14. The segments 20 are subsequently thermoset to curl in and form the dome shaped insertion tip 18. The head 46 of the tampon 12 is therefore located to the right in FIG. 1 of the ribs 32 of the barrel 14, within the insertion tip 18. The snap-action tampon ejecting mechanism 54 of the plunger 40 is adjacent the tampon head 46 and the gripping end 50 of the plunger protrudes from the gripping end 30 of the barrel 14. The stem 44 of the tampon 12 lies within the interior 42 of the plunger 40, The withdrawal string 73 from the tampon protruding from the open ends of the plunger 40 and the barrel 14. For assembly of the tampon in the applicator as described above, a thermoset material is needed for the barrel, particularly its insertion tip 18.

The tampon applicator 10 of the present invention is readied for use by a user gripping plunger 40 with one hand and barrel 14 by the other hand and retracting plunger 40 sufficiently to clear the tampon 12 from the interior 4 of plunger 40 while the tampon 12 is restrained from moving rearward by the barrel ribs 32. Further retraction of tee plunger 40 brings the forward tips 84 on the hinged panels 56 and 58 into engagement with the tapered steps 39 on the barrel 14 which forces the panels 56 and 58 to snap inwardly into the plunger 40, as shown in FIG. 10. The inwardly collapsed hinged panels 56 and 58 then define a solid contacting surface for bearing against the rear end of tampon 12. Note that if further retraction of the plunger 40 is attempted, the end stop tabs 80 and 82 engage the tabs 38 on the barrel 14 which helps prevent the plunger 40 from being accidentally pulled from the barrel 14.

After barrel 14 is inserted into the catamenial canal, the plunger 40 is then pushed forward to eject tampon 12 through the flexible and easily yielding triangular segments 20 of the insertion tip 18 of barrel 14. The inwardly biased triangular segments 20 of barrel 14 press tightly against tampon 12 while the tampon 12 is being ejected. This prevents pinching of sensitive tissue or other discomfort during the insertion process.

FIG. 8 shows the tampon 12 both while it is partially ejected (in phantom) and after it is entirely ejected from the barrel 14.

Although the present invention has been described in relation to a particular embodiment thereof, many other variations and modifications and other uses will become apparent to those skilled in the art. It is preferred, therefore, that the present invention be limited not by the specific disclosure herein, but only by the appended claims.

What is claimed is:

1. A tampon applicator, comprising: a barrel, and a plunger telescopically slidable within the barrel;

the plunger having a peripheral wall defining an interior for containing a tampon therein, the plunger having a tampon ejecting end for ejecting the tampon from the barrel and an actuating end by which the plunger is pressed for ejection of the tampon from the barrel, pivotable panel means hingedly supported on the wall of the plunger so as to snap inwardly into the interior of the plunger in response to a radially inwardly directed activating force applied thereto and including means for locking and retaining said panel means in said inward position upon the subsequent removal of the radially inwardly directed activating force; and the barrel being defined by a peripheral barrel wall and having an insertion end to be inserted, a barrel grasping end opposite the insertion end, and a tab at the grasping end of the barrel for engaging the pivotable panel means during retraction of the plunger through the barrel grasping end, for pushing inwardly upon the pivotable panel means to snap and lock it into the interior of the plunger.

2. The applicator of claim 1, wherein the panel means includes at least one pivotable panel disposed at the tampon ejecting end of the plunger.

3. A tampon applicator, comprising: a barrel, and a plunger telescopically slidable within the barrel;

the plunger having a peripheral wall defining an interior for containing a tampon therein, the plunger having a tampon ejecting end for ejecting the tampon from the barrel and an actuating end by which the plunger is pressed for ejection of the tampon from the barrel, pivotable panel means supported on the wall of the plunger so as to snap inwardly into the interior of the plunger in response to a radially inwardly directed force applied thereto; and the barrel being defined by a peripheral barrel wall and having an insertion end to be inserted, a barrel grasping end barrel for engaging the pivotable panel means during retraction of the plunger through the barrel grasping end, for pushing inwardly upon the pivotable panel means to snap it into the interior of the plunger and the panel means includes first and second panels which are each hingedly connected to the wall of the plunger.

4. The applicator of claim 3, wherein the peripheral wall of the plunger has an outer surface and wherein the first and second hinged panels are of a radial height to project beyond the outer surface of the plunger before the panels are deflected inward.

5. The applicator of claim 4, wherein the first and second hinged panels have connected side edges opposite their respective hinged edges and the connected side edges engage to resist moving inward and upon application of inward force to the panels, the connected edges interact to cause the panels to snap into the inside of the plunger.

6. The applicator of claim 3, wherein each the first and second hinged panels are chevron-shaped.

7. The applicator of claim 3, wherein the tab on the barrel includes a step tapered radially for smoothly engaging the first and second hinged panels and the taper is oriented to move the panels radially inward as the plunger is retracted from the barrel.

8. The applicator of claim 1, further comprising restraining means for restraining a tampon disposed in the barrel against moving toward the barrel grasping end of the barrel during retraction of the plunger.

9. The applicator of claim 8, wherein the restraining means comprises at least one rib on the interior of the barrel wall and facing the plunger.

10. A tampon applicator, comprising: a barrel, and a plunger telescopically slidable within the barrel;

the plunger having a peripheral wall defining an interior for containing a tampon therein, the plunger having a tampon ejecting end for ejecting the tampon from the barrel and an actuating end by which the plunger is pressed for ejection of the tampon from the barrel, pivotable panel means supported on the wall of the plunger so as to snap inwardly into the interior of the plunger in response to a radially inwardly directed force applied thereto; and the barrel being defined by a peripheral barrel wall and having an insertion end to be inserted, a barrel grasping end opposite the insertion end, and a tab at the grasping end of the barrel for engaging the pivotable panel means during retraction of the plunger through the barrel grasping end, for pushing inwardly upon the pivotable panel means to snap it into the interior of the plunger;

restraining means for restraining a tampon disposed in the barrel against moving toward the barrel grasping end of the barrel during retraction of the plunger;

the restraining means comprises at least one rib on the interior of the barrel wall and facing the plunger and the at least one rib comprises a plurality of circumferentially spaced ribs extending from the insertion end of the barrel to the grasping end thereof.

11. The applicator of claim 10, wherein the tab in the barrel is disposed between the restraining ribs.

12. In combination, the applicator of claim 11, and a tampon having a stem and an enlarged head disposed in the insertion tip, the restraining means being positioned for engaging the head of the tampon to prevent the head from sliding rearwardly into the barrel beyond the insertion tip.

13. The applicator of claim 1, wherein the insertion end of the barrel comprises a plurality of inwardly biased petal shaped panels for forming an insertion tip.

14. The applicator of claim 1, further comprising end stop means for preventing complete separation of the plunger from the barrel during retraction of the plunger.

15. The applicator of claim 14, wherein the end stop means comprises at least one end stop tab on the peripheral wall of the plunger adjacent the hinged panels and in position to engage the tab means on the barrel.

* * * * *